(12) United States Patent
Huber

(10) Patent No.: US 6,573,269 B1
(45) Date of Patent: Jun. 3, 2003

(54) PYRIMIDINE-2,4,6-TRIONE LIGHT SCREENING COMPOSITIONS

(75) Inventor: Ulrich Huber, Erlenbach (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/654,595

(22) Filed: Sep. 1, 2000

(30) Foreign Application Priority Data

Sep. 1, 1999 (EP) ............................................. 99117187

(51) Int. Cl.⁷ ................... C07D 239/02; A61K 31/515; A61K 7/44; A61K 6/00; F21V 9/04
(52) U.S. Cl. ......................... 514/270; 544/306; 556/9; 252/589; 424/59; 424/60; 424/400; 424/401
(58) Field of Search .................. 514/270; 544/306; 556/9; 252/589; 424/59, 60, 400, 401

(56) References Cited

U.S. PATENT DOCUMENTS 5,561,179 A    10/1996   Borzatta et al. ............... 524/99
6,114,546 A    9/2000    Yasuda et al. ............... 549/285

FOREIGN PATENT DOCUMENTS

| JP | 11-80130 | * | 3/1999 |
| JP | 11-116556 | | 4/1999 |
| WO | WO 98/14423 | | 4/1998 |

OTHER PUBLICATIONS

Chemical Abstracts, vol. 130, No. 24 of JP 11116556 (1999).
Chemical Abstracts, vol. 130, No. 19 of JP 01180130 (1989).
Chemical Abstracts, vol. 131, No. 17 of JP 11263778 (1999).

* cited by examiner

Primary Examiner—John M. Ford
Assistant Examiner—Tamthom N. Truong
(74) Attorney, Agent, or Firm—Bryan Cave LLP

(57) ABSTRACT

The present invention provides compounds of formula I, which are effective in absorbing ultraviolet radiation and can be used as sunscreen agents:

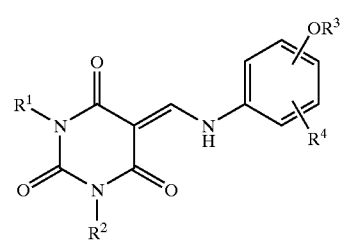

wherein $R^1$ and $R^2$ are each independently $C_2$–$C_{18}$ alkyl, $C_5$–$C_7$ cycloalkyl, or $C_2$–$C_{18}$ alkyl in which at least one methylene group is replaced by oxygen;

$R^3$ is hydrogen, $C_1$–$C_{18}$ alkyl, $C_2$–$C_{18}$ alkyl in which at least one methylene group is replaced by oxygen, $C_1$–$C_{18}$ alkyl carbonyl, $C_3$–$C_{18}$ alkenyl, $C_3$–$C_{18}$ alkynyl, or a group YS;

$R^4$ is hydrogen, $C_1$–$C_8$ alkyl or a group $OR^3$;

Y is a linker group; and

S is a silane-, an oligosiloxane- or a polysiloxane-moiety.

18 Claims, No Drawings

PYRIMIDINE-2,4,6-TRIONE LIGHT SCREENING COMPOSITIONS

FIELD OF THE INVENTION

The present invention relates to novel pyrimidine-2,4,6-trione compounds which are effective in absorbing ultra violet radiation and to light screening compositions containing such pyrimidine-2,4,6-trione compounds.

BACKGROUND OF THE INVENTION

Light screening compositions containing pyrimidine-2,4,6-trione compounds are described in WO 98/14423. This publication refers, inter alia, to compounds of the general formula:

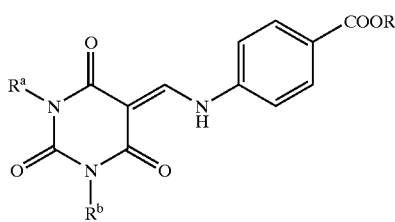

wherein

R is alkyl, cyclic alkyl, aralkyl or aryl; and $R^a$ and $R^b$ are each independently hydrogen, alkyl, cyclic alkyl, aralkyl and aryl.

This publication discloses that such compounds have an excellent ultraviolet absorbing ability. These compounds, however, are sensitive to hydrolytic decomposition.

SUMMARY OF THE INVENTION

It has now been found that compounds of the above formula in which the —COOR group is replaced by an ether group —OR or an ester group —OCOR surprisingly exhibit superior chemical stability.

Thus, one embodiment of the invention are compounds of the general formula I

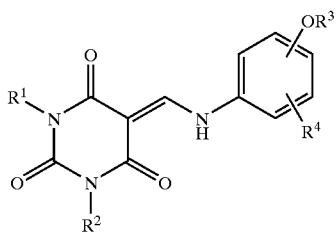

wherein $R^1$ and $R^2$ are each independently $C_2$–$C_{18}$ alkyl, $C_5$–$C_7$ cycloalkyl or $C_2$–$C_{18}$ alkyl in which at least one methylene group is replaced by oxygen;

$R^3$ is hydrogen, $C_1$–$C_{18}$ alkyl, $C_2$–$C_{18}$ alkyl in which at least one methylene group is replaced by oxygen, $C_1$–$C_{18}$ alkyl carbonyl, $C_3$–$C_{18}$ alkenyl, $C_3$–$C_{18}$ alkynyl, or a group YS;

$R^4$ is hydrogen, $C_1$–$C_8$ alkyl or a group $OR^3$;

Y is a linker group; and

S is a silane-, an oligosiloxane- or a polysiloxane moiety.

Another embodiment of the invention are light screening compositions containing a compound of formula I.

A further embodiment of the invention is a method for protecting a surface of a substrate from ultraviolet light. This method includes applying to a surface of a substrate a UV-blocking amount of a light screening composition containing a cosmetic base and a compound of formula I.

DETAILED DESCRIPTION OF THE INVENTION

In the compounds of formula I, $R^1$ and $R^2$ may be the same or different. Preferably, $R^1$ and $R^2$ have the same meaning and are ethyl, propyl, isopropyl, n-butyl, sec. butyl, tert. butyl, 2-ethyl hexyl or cyclohexyl. Particularly preferred is isopropyl.

The residue $OR^3$ is preferably in the para position. $R^3$ preferably is $C_2$–$C_8$ alkyl or a group YS, more preferably 2-ethyl hexyl or a group YS.

The residue $R^4$ preferably is hydrogen or hydroxy.

In the present invention, the term "$C_1$–$C_{18}$ alkyl" means straight chain or branched saturated hydrocarbon residues with 1 to 18 carbon atoms such as methyl, ethyl, propyl, isopropyl, thexyl, (1,1,2 trimethyl-1-propyl), n-butyl, sec. butyl, tert. butyl, pentyl, neopentyl, hexyl, 2-ethyl-hexyl, octyl and the like.

The term "$C_5$–$C_7$ cycloalkyl" means saturated hydrocarbon rings with 5 to 7 carbon atoms, i.e. cyclopentyl, cyclohexyl, and cycloheptyl.

The term "$C_2$–$C_{18}$ alkyl in which at least one methylene group is replaced by oxygen" means straight chain or branched saturated hydrocarbon residues with up to 17 carbon atoms which are bound via a carbon atom and have at least one group such as —(CH$_2$—O)—, —(CH$_2$—CH$_2$—O)—, —(CH$_2$—CH$_2$—CH$_2$—O)—, —(CH$_2$—CH$_2$—CH$_2$—CH$_2$—O)—, and the like.

In the term "$C_1$–$C_{18}$ alkyl carbonyl," the alkyl residue is as defined above.

The term "$C_3$–$C_{18}$ alkenyl" means straight chain or branched unsaturated hydrocarbon residues with 3 to 18 carbon atoms containing at least one double bond such as propen-2-yl, propen-3-yl, buten-3-yl, buten-4-yl, penten-4-yl, penten-5-yl, and the like.

The term "$C_3$–$C_{18}$ alkynyl" means straight chain or branched unsaturated hydrocarbon residues with 3 to 18 carbon atoms containing at least one triple bond. A preferred alkynyl residue is propargyl.

As used herein, the phrase "linker group" means a $C_3$–$C_{12}$ divalent alkylene or alkylene chain which links the UV absorbing chromophoric residue to the silane, oligosiloxane or polysiloxane moiety.

The term "$C_3$–$C_{12}$ divalent alkylene chain" means straight chain or branched saturated hydrocarbon residues such as 3-propylene, 2-propylene, 2-methyl-3-propylene, 3-butylene, 4-butylene, 4-pentylene, 5-pentylene, 6-hexylene, and the like.

The term "$C_3$–$C_{12}$ divalent alkenylene chain" means unsaturated hydrocarbon residues containing at least one double bond, such as for example, 2-propen-2-ylene, 2-propen-3-ylene, 3-buten-3-ylene 3-buten-4-ylene, 4-penten-4-ylene, 4-penten-5-ylene, (3-methyl)-penta-2,4-dien-4 or 5-ylene, 11-dodecen-11-ylene, and the like.

The divalent alkylene or alkenylene chains may be interrupted by one or several oxygen atoms. Examples of oxygen interrupted linker groups are e.g. 2-ethyloxy-eth-2-ylene, 4-butyloxy-eth-2-ylene or 3,6-dioxa-8-octylen. The linker groups of the present invention include 3-propylene, 4-butylene, 2-propen-2-ylene, 2-propen-3-ylene or 3-buten-4-ylene, preferably 2-propen-2-ylene or 2-propen-3-ylene.

The term "silane" means a group —SiR$^5$R$^6$R$^7$, wherein R$^5$, R$^6$ and R$^7$ are each independently C$_1$–C$_6$ alkyl or phenyl. Preferred silane groups are e.g. trimethylsilane, triethylsilane, tripropylsilane, triisopropylsilane, dimethyl tert.butylsilane, dimethyl thexylsilane, triphenylsilane, dimethylphenylsilane and the like.

As used herein, the term "oligosiloxane" means groups of the general formula —SiR$^8_m$(OSiR$^{8'}_3$)$_n$ where m=0, 1 or 2; n=1, 2 or 3, m+n=3, and wherein R$^{8'}$ are each independently C$_1$–C$_6$ alkyl or phenyl. Preferably R$^8$ and R$^{8'}$ have the same meaning. Preferably, the oligosiloxane is —SiMe(OSiMe$_3$)$_2$, wherein Me is methyl.

As used herein, the term "oligosiloxane" also includes groups of formulae IIa or IIb:

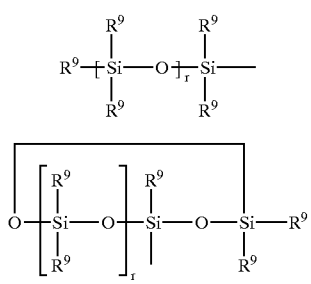

IIa

IIb wherein R$^9$ is C$_1$–C$_6$ alkyl or phenyl and r is an integer from 1 to 9, preferably 1 to 3. The residue R$^9$ is preferably C$_1$–C$_4$ alkyl, such as for example, methyl.

As used herein, the term "polysiloxane" means groups of formulae IIIa or IIIb:

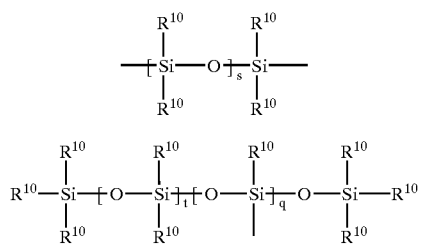

IIIa

IIIb wherein

R$^{10}$ is C$_1$–C$_6$ alkyl or phenyl;

s is an integer from 4 to 250;

t is an integer from 5 to 250; and q is an integer from 1 to 30.

Preferably, "s" is an integer from 4 to 150. Preferably, "q" is an integer from 2 to 10, such as for example, it has statistical mean value of about 4. Preferably, "t" is an integer from 5 to 150, such as for example, it has statistical mean value of about 60. The residue R$^{10}$ is preferably C$_1$–C$_4$ alkyl, such as for example, methyl.

The compounds of the general formula I may be prepared by methods known per se. For example, in compounds of the general formula I, wherein R$^3$ is C$_1$–C$_{18}$ alkyl, C$_2$–C$_{18}$ alkyl in which at least one methylene group is replaced by oxygen, C$_3$–C$_{18}$ alkenyl or C$_3$–C$_{18}$ alkynyl, and R$^4$ is hydrogen or C$_1$–C$_8$ alkyl, the process starts by alkylation of a nitrophenol of the formula IVa:

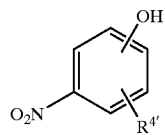

wherein R$^{4'}$ is hydrogen or C$_1$–C$_8$ alkyl; with an alkyl halide to provide a nitro phenolic ether IVb as set forth below:

Step A

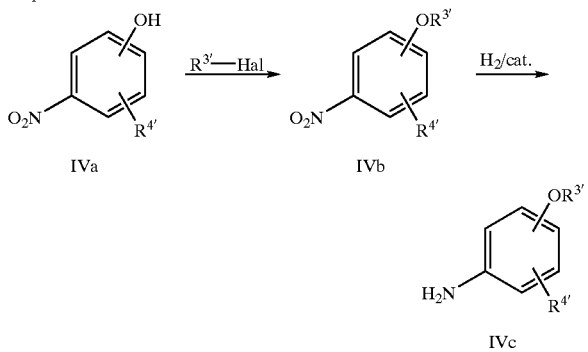

IVa

IVb

IVc

The alkyl halide has the formula R$^{3'}$ Hal, wherein

R$^{3'}$ is C$_1$–C$_{18}$ alkyl, C$_2$–C$_{18}$ alkyl in which at least one methylene group is replaced by oxygen, C$_3$–C$_{18}$ alkenyl or C$_3$–C$_{18}$ alkynyl; and Hal is chloro, bromo or iodo, preferably, chloro or bromo.

The starting nitrophenol is commercially available or may be readily prepared by known methods.

The reaction is run in a suitable reaction solvent. The choice of the solvent is not critical. Suitable solvents include toluene, pyridine or polar aprotic solvents, such as e.g., 1-methyl-2-pyrrolidone, dimethylformamide, dimethylsulfoxide, dioxane, tetrahydrofuran, acetonitrile, and the like. The reaction mixture includes an acid acceptor, such as a mild base, for example, sodium or potassium carbonate, which can absorb the acid-by-product of the alkylation. The reactants usually are present in about equal molar amounts and the reaction is run at an elevated temperature, e.g. at about 80° C.–150° C., preferably at about 100° C.

The nitro phenolic ether (IVb) obtained is then reduced either by conventional methods using reduction with tin or zinc and hydrochloric acid or by catalytic hydrogenation to afford the corresponding amino group to provide the p-amino phenolic ether of the formula IVc. The catalytic hydrogenation is employed, using conventional catalysts such as Raney-nickel, palladium or platinum. The catalytic hydrogenation is carried out at temperatures in the range of 0° C. to about 100° C., preferably at about 20° C. to about 60° C., such as for example, at about 40° C. and under atmospheric pressure to about 100 bar, preferably at about 20 bar to about 60 bar, such as for example, at about 40 bar.

Nitro phenolic ether compounds wherein R$^3$, is C$_3$–C$^{18}$ alkenyl or C$_3$–C$_{18}$ alkynyl are preferably reduced using tin and hydrochloric acid.

Compounds of the general formula I, wherein R$^3$ is C$_1$–C$_{18}$ alkyl, C$_2$–C$_{18}$ alkyl in which at least one methylene group is replaced by oxygen, C$_3$–C$_{18}$ alkenyl or C$_3$–C$_{18}$ alkynyl and R$^4$ is a group OR$^{3'}$ may also be prepared.

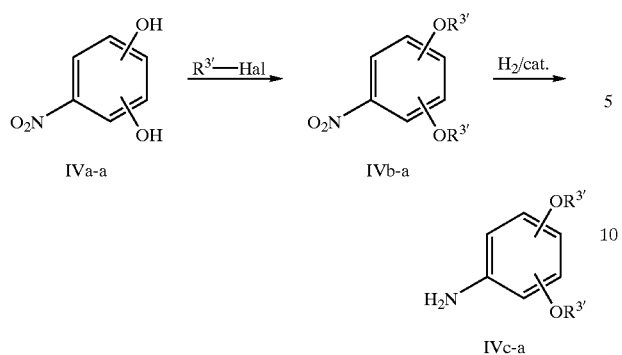

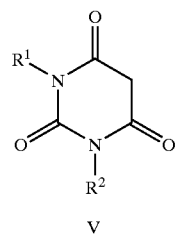

V

Other methods to prepare the pyrimidine-2,4,6-trione residue of the general formula V, starting from e.g. malonic ester and dialkyl urea are described in WO 95/00112.

Finally, residue V is linked with residue IV by condensation in the presence of trialkyl orthoformate, preferably triethyl orthoformate $(CH(OC_2H_5)_3)$ to form compound VII:

Step C

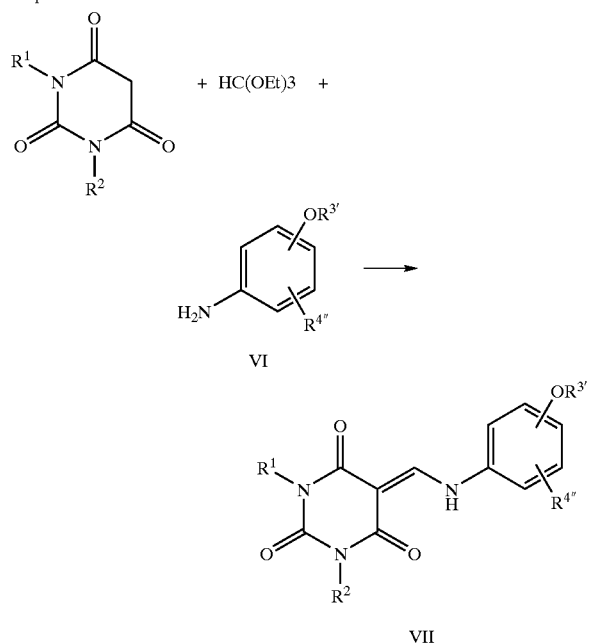

VII

The group $R^{3'}$ is as defined above.

Compounds of the general formula I, wherein $R^3$ is $C_1$–$C_{18}$ alkyl, $C_2$–$C_{18}$ alkyl in which at least one methylene group is replaced by oxygen, $C_3$–$C_{18}$ alkenyl or $C_3$–$C_{18}$ alkynyl and $R^4$ is hydroxy ($OR^3$ with $R^3$=H) may be prepared using a conventional protective group for the hydroxy group such as e.g. ether-type protective groups or acetal-type protective groups.

Compounds of the general formula I, wherein $R^3$ is hydrogen and $R^4$ is hydrogen or $C_1$–$C_8$ alkyl may be prepared by reducing the corresponding nitro phenol IVa-b using conventional methods.

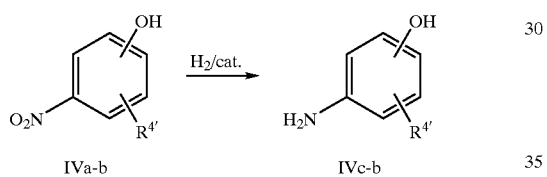

$R^{4'}$ is as defined above.

The pyrimidine-2,4,6-trione residue of the general formula V:

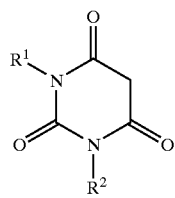

V wherein $R^1$ and $R^2$ are as defined above may be prepared as set forth below be adding malonic acid in an equimolar quantity to a carbodiimide of the general formula $R^1$—N=C=N—$R^2$, wherein $R^1$ and $R^2$ are as defined above. The reaction is run in a suitable reaction solvent. The choice of the solvent is not critical. Preferred solvents are polar aprotic solvents as listed above.

Step B

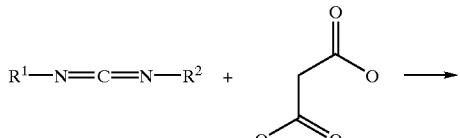

wherein $R^1$, $R^2$ and $R^{3'}$ are as defined above, and $R^{4''}$ is hydrogen, $C_1$–$C_8$ alkyl or $OR^{3'}$.

The condensation is carried out in a solvent at reflux temperatures for several hours. The choice of the solvent is not critical. Preferred solvents are polar aprotic solvents as listed above.

For preparing a compound of the general formula I, it is also possible to first prepare an intermediate of the general formula VIIa:

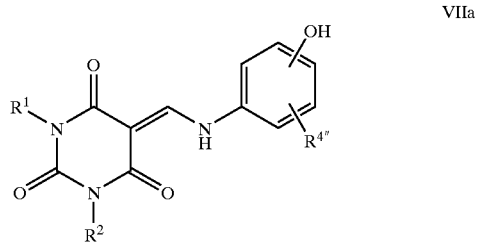

VIIa wherein $R^1$, $R^2$ and $R^{4''}$ are as defined above by reacting a amino phenol with a pyrimidine 2,4,6-trione compound in the presence of trialkyl orthoformate, preferably triethyl orthoformate (CH(OC$_2$H$_5$)$_3$) and then alkylating the resulting intermediate of the formula VIIa.

Compounds of the general formula I, wherein R$^3$ is C$_1$–C$_{18}$ alkyl carbonyl and R$^4$ is hydrogen or C$_1$–C$_8$ alkyl may be prepared by acylating the compound of formula VIIa using known esterification reactions.

Compounds of formula I containing a silane-, an oligosiloxane- or a polvsiloxane moiety are prepared by hydrosilation. The following reaction scheme shows an example of how to prepare a compound of formula I wherein R$^3$ is a group YS, S is a an oligosiloxane of the formula —SiR$^{8m}$(OSiR$^{8'}_3$)$_n$, m=0 1 or 2; n=1, 2 or 3, and m+n=3, wherein R$^{8'}$ are each independently C$_1$–C$_6$ alkyl or phenyl and R$^{4'}$ is as defined above, namely hydrogen or C$_1$–C$_8$ alkyl.

Step A

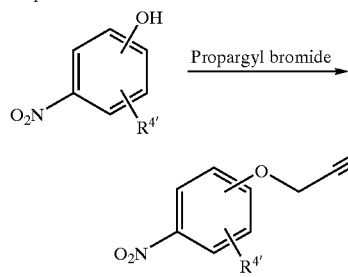

Step B

R$^1$—N=C=N—R$^2$ +

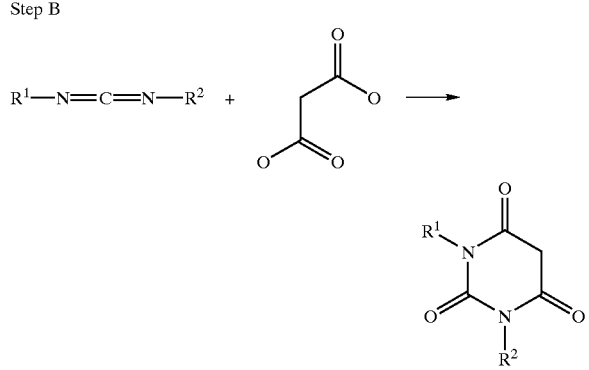

Step C

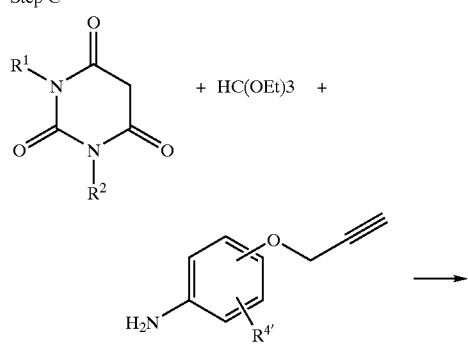

-continued

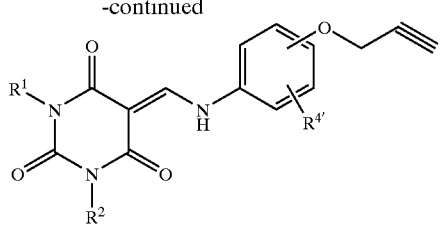

Step D

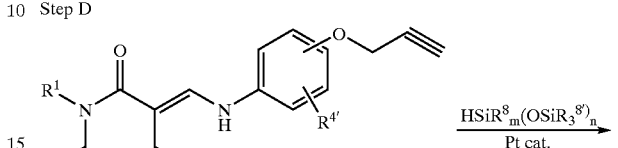

The hydrosilation reaction between the SiH group and the alkynyl group (step D) is carried out in the presence of a transition metal catalyst, e.g. platinum on charcoal or a platinum complex catalyst, such as e.g. divinyl-tetramethyl disiloxane platinum complex. The reaction is run in a suitable reaction solvent, such as e.g. in toluene. The reactants usually are present in about equal molar amounts and the reaction is run at a somewhat elevated temperature, e.g. at about 60° C.–150° C., preferably at about 40° C.–100° C., such as for example, at about 80° C.

Compounds of formula I containing an oligosiloxane moiety of formula IIa or IIb or a polysiloxane moiety of formula IIIa or IIIb are prepared accordingly. The reaction partner is the corresponding SiH containing oligosiloxane or polysiloxane moiety.

The compounds of formula I have adsorption maxima in the range of 320 nm to 400 nm, the so called UV-A radiation.

The preparation of novel light screening agents, especially of preparations for skin protection and, respectively, sunscreen preparations for everyday cosmetics, includes incorporating a compound of formula I in a cosmetic base which is conventional for light screening agents. Where convenient, other conventional UV-A, and/or UV-B filters may also be combined in the light screening composition during this incorporation. The combination of UV filters may show a synergistic effect. Preparation of the light screening agents is well known to the skilled artisan in this field. The amount of compounds of formula I and other known UV-filters in the light screening compositions of the present invention is not critical. Suitable amounts are about 0.5 to about 12%.

Suitable UV-B filters for use in the present invention are substances having absorption maxima between about 290 and 320 nm, such as for example the following organic compounds:

Acrylates, such as 2-ethylhexyl 2-cyano-3,3-diphenylacrylate (octocrylene, PARSOL 340), ethyl 2-cyano-3,3-diphenylacrylate, and the like;

Camphor derivatives, such as 4-methyl benzylidene camphor (PARSOL 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid, and the like;

Cinnamate derivatives, such as octyl methoxycinnamate (PARSOL MCX), ethoxyethyl methoxycinnamate, diethanolamine methoxycinnamate (PARSOL Hydro), isoamyl methoxycinnamate and the like, as well as cinnamic acid derivatives bond to siloxanes;

Organosiloxane compounds containing benzmalonate groups as recited in EP 0358584 B1, EP 0538431 B1 and EP 0709080 A1;

Pigments, such as microparticulated $TiO_2$, and the like. As used herein, the term "microparticulated" refers to a particle size from about 5 nm to about 200 nm, particularly from about 15 nm to about 100 nm. The $TiO_2$ particles may also be coated by metal oxides, such as e.g. aluminum or zirconium oxides or by organic coatings such as e.g. polyols, methicone, aluminum stearate, alkyl silane. Such coatings are well known in the art.

Imidazole derivatives, such as e.g. 2-phenyl benzimidazole sulfonic acid and its salts (PARSOL HS). Salts of 2-phenyl benzimidazole sulfonic acid are e.g. alkali salts such as sodium- or potassium salts, ammonium salts, morpholine salts, salts of primary, sec. and tert. amines such as monoethanolamine salts, diethanolamine salts, and the like;

Salicylate derivatives, such as isopropylbenzyl salicylate, benzyl salicylate, butyl salicylate, octyl salicylate (NEO HELIOPAN OS), isooctyl salicylate or homomenthyl salicylate (homosalate, HELIOPAN), and the like;

Triazone derivatives, such as octyl triazone (UVINUL T-150), dioctyl butamido triazone (UVASORB HEB), and the like.

Suitable UV A filters for use in the present invention are substances having absorption maxima between about 320 and 400 nm, such as the following:

Dibenzoylmethane derivatives, such as 4-tert. butyl-4'-methoxydibenzol-methane (PARSOL 1789), dimethoxydibenzoylmethane, isopropyldibenzoylmethane and the like;

Benzotriazole derivatives, such as 2,2'-methylene-bis-(6-(2H-benzotriazole-2-yl)-4-(1,1,3,3, -tetramethylbutyl)-phenol (TINOSORB M), and the like;

Pigments, such as microparticulated ZnO, and the like. The term "microparticulated" refers to a particle size from about 5 nm to about 200 nm, particularly from about 15 nm to about 100 nm. The ZnO particles may also be coated by metal oxides such as e.g. aluminum or zirconium oxides or by organic coatings such as e.g. polyols, methicone, aluminum stearate, alkyl silane. Such coatings are well known in the art.

Because dibenzoylmethane derivatives are photolabile, it is necessary to photostabilize these UV-A screening agents. Thus, the term "conventional UV-A screening agent" as used herein also refers to dibenzoylmethane derivatives, such as e.g. PARSOL 1789 stabilized by the following stabilizing agents:

3,3-Diphenylacrylate derivatives as described in EP 0 514 491 B1 and EP 0 780 119 A1;

Benzylidene camphor derivatives as described in Deflandre, et al., U.S. Pat. No. 5,605,680;

Organosiloxanes containing benzmalonate groups as described in EP 0358584 B1, EP 0538431 B1 and EP 0709080 A1.

As used herein, "cosmetic bases" for light screening compositions include any conventional preparation which corresponds to the desired cosmetic requirements, e.g. creams, lotions, emulsions, salves, gels, solutions, sprays, sticks, and milks. See, Sunscreens, Development, Evaluation and Regulatory Aspects, ed. N. Y. Lowe, N. A. Shaath, Marcel Dekker, Inc. New York and Basel, 1990.

Having regard to their good lipophilicity, the compounds of formula I may be incorporated well into oil and fat containing cosmetic preparations.

The following examples are provided to further illustrate the processes and compositions of the present invention. These examples are illustrative only and are not intended to limit the scope of the invention in any way.

EXAMPLES

Example 1

5-{[4-(2-Ethyl-hexyloxy)-phenylamine]-methylene}-1,3-diisopropyl-pyrimidine-2,4,6-trione

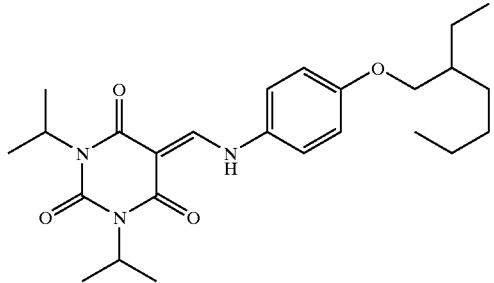

a) 4-Nitrophenyl-(2-ethyl-hexyl)-ether

In a 300 ml three necked reaction flask equipped with a reflux condenser, a thermometer, and a magnetic stirrer, 27.7 g of p-nitrophenol and 52.7 g of anhydrous sodium carbonate were suspended in 180 ml 1-methyl-2-pyrolidone under a nitrogen atmosphere. 48 ml of 2-ethyl-hexylbromide were added by means of a dropping funnel. The reaction mixture was heated to 100° C. for 180 minutes. Then, the mixture was poured into water and extracted four times with ethyl acetate. The combined organic phases were washed with 1 N NaOH and with a NaCl solution, dried with $Na_2SO_4$ followed by concentration on a rotary evaporator. The product was freed of the residual 2-ethyl-hexylbromide by heating to 60° C. at a high vacuum of 0.5 mbar. Yield 32.7 g (69% of the theory) of a clear yellow liquid. MS: 192(M+), 163, 113, 83, 71,57(100%).

b) 4-(2-Ethyl-hexyloxy)-phenylamine

A 600 ml hydrogenation autoclave was charged with 36 g(0.143 mol) of the above p-nitro phenolic ether and with 5 g of wet Raney Ni catalyst in 50 ml methanol. The reduction was carried out for 18 hours at 40° C. and a hydrogen pressure of 40 bar. The mixture was filtered and concentrated, followed by a flash chromatography in hexane/ethyl acetate=9:1 and "Kugelrohr" distillation (200° C./0.8 mbar). Yield 8.8 g of a brownish liquid.

c) 1,3-diisopropyl-pyrimidine-2,4,6-trione.

13.4 g of malonic acid was suspended in 130 ml of tetrahydrofuran in a 500 ml reaction flask and cooled to 0° C. A solution of 32.6 g of N,N'-diisopropyl-carbodiimide in 130 ml of tetrahydrofuran was slowly added within 45 minutes at 0° C. to 5° C. followed by stirring for 2 hours at this temperature. The reaction mixture was concentrated at a rotary evaporator and recrystallized in cyclohexane and then in hexane. Yield 20.6 g (75% of the theory) of slightly yellowish crystals, m.p. 145–148° C.

d) 5-{[4-(2-ethyl-hexyloxy)-phenylamine]-methylene}-1,3-diisopropyl-pyrimidine-2,4,6-trione.

A 100 ml three necked reaction flask equipped with a thermometer, a reflux condenser, and a magnetic stirrer under nitrogen atmosphere was charged with 1.1 g (5 mmol) of 4-(2-ethyl-hexyloxy)-phenylamine (Example 1b), 1.06 g (5 mmol) of 1,3-diisopropyl-pyrimidine-2,4,6-trione (Example 1c) and 11.1 g (75 mmol) of triethyl orthoformate in 10 ml of tetrahydrofuran. This mixture was refluxed for 18 hours followed by washing twice with water, dried with $Na_2SO_4$, and concentrated on a rotary evaporator. The raw product was recrystallized in ethanol to yield 0.84 g of yellowish crystals. M.p. 74–76° C., UV 355 nm (32,122). This product was irradiated in high dilution with a Hg-lamp (150 W from Hereus) and was shown to be photostable.

e) Measurement of solubility in Cétiol LC (cocoyl caprylate caprate) and Crodamol DA (diisopropyl adipate).

Oversaturated solutions of 5-{[4-(2-ethyl-hexyloxy)-phenylamine]-methylene}-1,3-diisopropyl-pyrimidine-2,4,6-trione (see 1d above) in the above solvents were prepared and treated in an ultrasonic bath for five minutes. After standing overnight at 25° C., the solution was filtered through a microfilter (Millipore, pore size 0.5 , μm), followed by UV measurement in $CH_2Cl_2$. The extinctions were compared with the extinctions of the pure compound. The solubilities were found to be 15.5% in Cétiol LC and 26.9% in Crodamol DA.

Example 2

5-{(4-Propargyloxy-phenylamine)-methylene}-1,3-diisopropyl-pyrimidine-2,4,6-trione

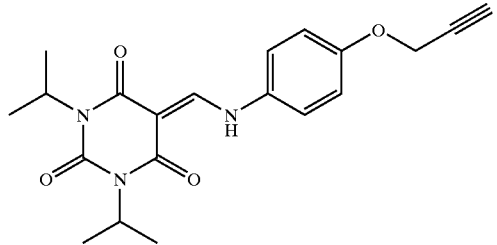

a) 4-Nitrophenyl-propargylic-ether

In a 200 ml three necked reaction flask equipped with a reflux condenser, a thermometer, and a magnetic stirrer, 20 g of p-nitrophenol and 38 g of anhydrous sodium carbonate were suspended in 90 ml 1-methyl-2-pyrolidone under a nitrogen atmosphere. 17.3 ml of propargyl bromide were added by means of a dropping funnel. The reaction mixture was heated to 100° C. for 60 minutes. Then the mixture was poured into water and extracted four times with ethyl acetate. The combined organic phases were washed with 1 N NaOH and with a NaCl solution, dried with $Na_2SO_4$ followed by concentration on a rotary evaporator to form 23.6 g of raw product. The product was recrystallized in isopropanol. Yield 21.8 g (85% of the theory) of yellowish crystals, m.p. 113–116° C.

b) 4-Propargyloxy-phenylamine

A 1 liter four necked reaction flask equipped with a thermometer, a reflux condenser, and a magnetic stirrer was charged with 21 g (118 mmol) of 4-nitrophenyl-propargylic-ether (Example 2a) in 295 ml of methanol. 295 ml of concentrated hydrochloric acid was slowly added with rigorous stirring, followed by slow addition of 59 g of tin powder. After this addition, the reaction temperature was kept at 60° C. for 2 hours. The mixture was poured into a solution of 295 g of sodium hydroxide in 1.2l of water. Methanol was distilled off on a rotary evaporator. The suspension was filtered and washed with ethanol. The filtrate was concentrated and distilled in the Kugelrohr apparatus at 180° C./0.07 mbar to yield 10.2 g of product. This was recrystallized in a little ethanol to yield 6.8 g of white crystals of pure product. MS: 147(M+), 108 (100%), 80,53.

c) 5-{(4-Propargyloxy-phenylamine)-methylene}-1,3-diisopropyl-pyrimidine-2,4,6-trione.

A 50 ml three necked reaction flask equipped with a thermometer, a reflux condenser, and a magnetic stirrer under a nitrogen atmosphere was charged with 1.45 g (10 mmol) of 4-propargyloxy-phenylamine (Example 2b), 2.1 g (10 mmol) of 1,3-diisopropyl-pyrimidine-2,4,6-trione (Example 1c), and 2.5 ml of triethyl orthoformate in 15 ml of tetrahydrofuran. This mixture was refluxed for 3.5 hours followed by concentrating on a rotary evaporator. The raw product was recrystallized in toluene and hexane to yield 2.9 g of yellow crystals. M.p. 110–114° C., UV 352 nm (31, 596). This product was irradiated in high dilution with a Hg-lamp (150 W from Hereus) and has been shown to be photostable.

Example 3

5-{[4-(2-(1,3,3,3-tetramethyl-1-[(trimethylsilyl)-oxy]-disiloxanyl)-prop-2-enyloxy)-phenylamine]-methylene}-1,3-diisopropyl-pyrimidine-2,4,6-trione

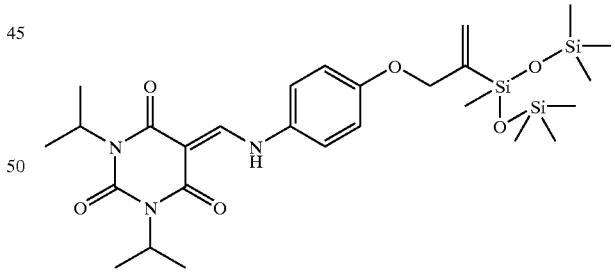

Hydrosilylation Reaction 550 mg of the above 5-{(4-propargyloxy-phenylamine)-methylene}-1,3-diisopropyl-pyrimidine-2,4,6-trione (Example 2c), 330 mg of 1,1,1,3,5,5,5-heptamethyl trisiloxane and a catalytic amount of divinyl-tetramethyl disiloxane platinum complex in 10 ml of toluene was placed in a three-necked reaction flask under an inert atmosphere and stirred for 20 hours at 80° C. The product solution was washed with a mixture of water/methanol=1:10 and concentrated to yield 920 mg. This product was chromatographed in hexane/ethylacetate 7:1 to yield 650 mg (76% of the theory) of a honey-like liquid. UV 354 nm (ε=31,520), MS:

591 (M+), 576, 551, 331 (100%) and 221. Its NMR shows a mixture of the vicinal and the geminal hydrosilylation product=1.3. It has an unlimited solubility in the cosmetic solvents tested above and excellent photostability qualities in high dilution, determined as described in Example 1.

Example 4

A polysiloxane was prepared which corresponds in its statistical mean to the following formula:

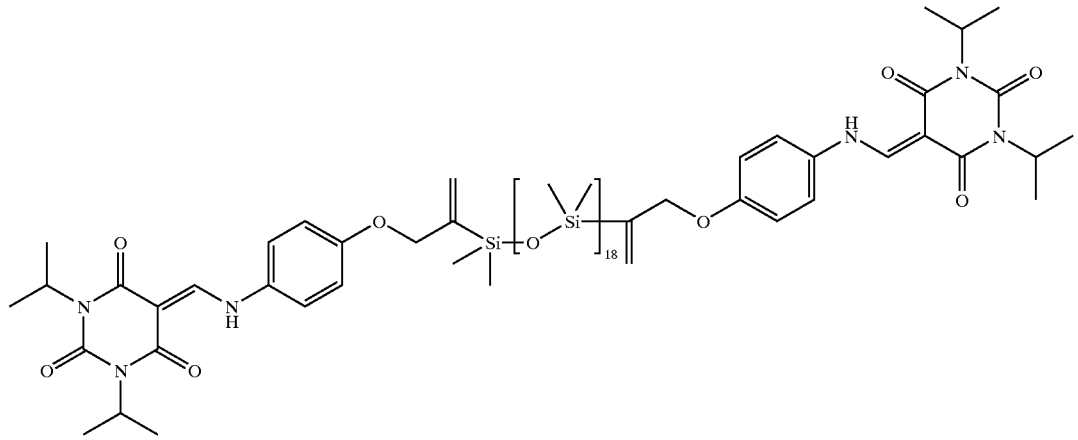

370 mg of 5-{(4-propargyloxy-phenylamine)-methylene}-1,3-diisopropyl-pyrimidine-2,4,6-trione (Example 2c), 810 mg of polysiloxane SLM/4 of Wacker-Chemie GmbH, and a catalytic amount of divinyl-tetramethyl disiloxane platinum complex in 10 ml of toluene was placed in a three-necked reaction flask under an inert atmosphere and heated for 11 days at 80° C. The product solution was washed with a mixture of water/methanol=1:10 and concentrated to yield 1170 mg (99%) of a dark liquid. UV 355 nm (E=237), having unlimited solubility in Cétiol LC and Crodamol DA and excellent photostability qualities in high dilution, determined as described in Example 1.

Example 5

A polysiloxane was prepared which corresponds in its statistical mean to the following formula:

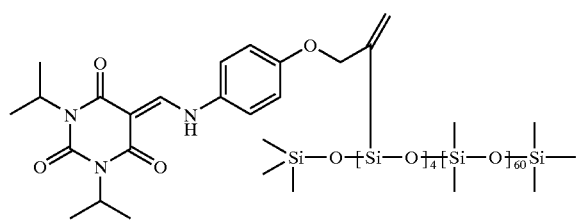

370 mg of 5-{(4-propargyloxy-phenylamine)-methylene}-1,3-diisopropyl-pyrimidine-2,4,6-trione (Example 2c), 1100 mg of polysiloxane Ae-9151 of Wacker-Chemie GmbH, and a catalytic amount of platinum carbon 5% in 10 ml of xylene was placed in a three-necked reaction flask tinder an inert atmosphere and heated for five days at 120° C. The product solution was filtered through Cellite, washed with a mixture of water/methanol=1:10 and concentrated to yield 1.4 g (95%) of a brownish oil. UV 355 nm (E=189), having unlimited solubility in Cétiol LC and Crodamol DA and excellent photostability qualities in high dilution, determined as described in Example 1.

Example 6

5-{(4-Hydroxy-phenylamine)-methylene}-1,3-diisopropyl-pyrimidine-2,4,6-trione

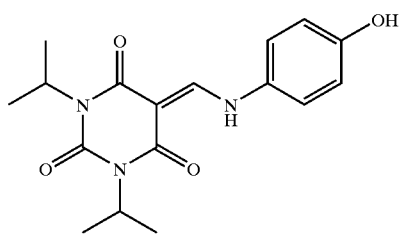

A 150 ml three necked reaction flask equipped with a thermometer, a reflux condenser, and a magnetic stirrer was charged under a nitrogen atmosphere with 3.3 g (30 mmol) of 4-aminophenol, 6.4 g (30 mmol) of 1,3-diisopropyl-pyrimidine-2,4,6-trione (Example 1c), and 7.11 g (50 mmol) of triethyl orthoformate in 60 ml of tert. butylmethyl ether. This mixture was refluxed for 5 hours followed by washing twice with water, dried with Na$_2$SO$_4$, and concentrated on a rotary evaporator. The yellow raw product was recrystallized from toluene/hexane to yield 9.5 g of yellow crystals (96% of the theory). M.p.172–173° C., UV 351 nm (27,911). This product was irradiated in high dilution with a Hg-lamp (150 W from Hereus) and has been shown to be photostable. The solubility in Crodamol DA was found to be 3.6%.

Example 7

5-{(2,4-Dihydroxy-phenylamine)-methylene}-1,3-diisopropyl-pyrimidine-2,4,6-trione

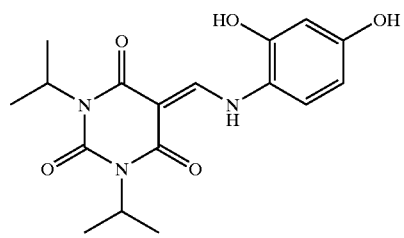

A 50 ml three necked reaction flask equipped with a thermometer, a reflux condensor, and a magnetic stirrer was charged under a nitrogen atmosphere with 3.0 g (19 mmol) of 2,4-dihydroxyaniline, 3.9 g (19 mmol) of 1,3-diisopropyl-pyrimidine-2,4,6-trione (Example 1c) and 5.7 g (39 mmol) of triethyl orthoformate in 15 ml of tert. butyl-methyl ether. This mixture was refluxed for 5.5 hours followed by washing twice with water, dried with $Na_2SO_4$ and concentrated on a rotary evaporator. The yellow raw product was recrystallized from toluene/hexane to yield 2.4 g of brown crystals. M.p. 225–226° C., UV 363 nm (23,564); This product was irradiated in high dilution with a Hg-lamp (150 W from Hereus) and has been shown to be photostable. The solubility in Crodamol DA was found to be 4.1%.

Example 8

5-{(4-Capryloxy-phenylamine)-methylene}-1,3-diisopropyl-pyrimidine-2,4,6-trione

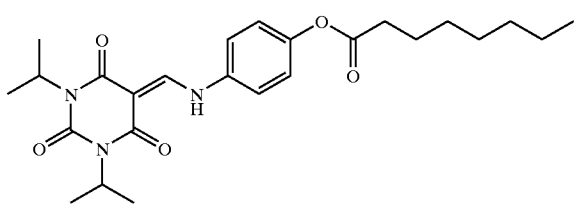

A 50 ml three necked reaction flask equipped with a thermometer, a reflux condensor, and a magnetic stirrer was charged under a nitrogen atmosphere with 1.66 g (5 mmol) of 5-{(4-hydroxy-phenylamine)-methylene}-1,3-diisopropyl-pyrimidine-2,4,6-trione (Example 6) and 0.48 g (6 mmol) of pyridine in 25 ml of dichloromethane. Then, 0.9 g (5.5 mmol) of caprylic acid chloride was slowly added. The reaction started exothermally. The reaction mixture was later heated to 75° C. for 22 hours. The mixture was washed twice w with each of 1 N HCl, a NaCl solution, and water and backwashed with dichloromethane, dried with $Na_2SO_4$, and concentrated on a rotary evaporator. The yellow slowly crystallizing oil was recrystallized from hexane to yield 3.2 g of yellowish crystals (70% of the theory). M.p.74–76° C., UV 346 nm (33,768). This product was also irradiated in high dilution with a Hg-lamp (150 W from Hereus) and has been shown to be photostable. The solubility in Crodamol DA was found to be 18.5 % and in Cétiol LC 6.6%.

Example 9

5-{[(2,4-Bis-Capryloxy)-phenylamine])-methylene}-1,3-diisopropyl-pyrimidine-2,4,6-trione and 5-{[(2-hydroxy-4-capryloxy)-phenylamine])-methylene}-1,3-diisopropyl-pyrimidine-2,4,6-trione

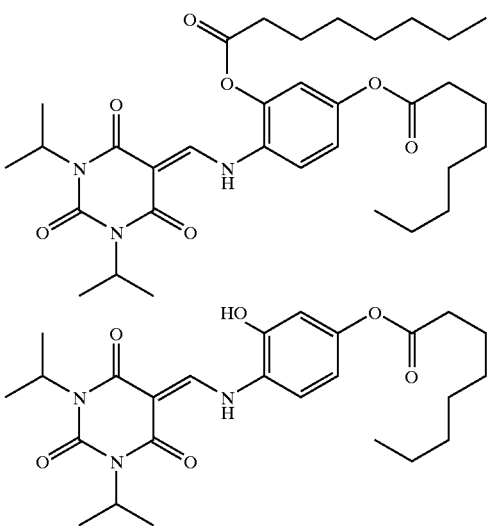

The reaction of Example 8 was repeated using the product of Example 7 (5-{(2,4-dihydroxy-phenylamine)-methylene}-1,3-diisopropyl-pyrimidine-2,4,6-trione). The resulting mixture was chromatographed in hexane/methyl-tert.butyl ether to yield two products, the diester in 85% yield, which was a yellowish honey, UV 351 nm (31,349) and easily mixable with Cétiiol LC in any proportion and the crystalline 5-{[(2-hydroxy-4-capryloxy)-phenylamine])-methylene}-1,3-diisopropyl-pyrimidine-2,4,6-trione in 15% yield, m.p. 115–117° C., UV 354 nm (25,813).

Example 10

A broad spectrum sunscreen lotion containing 2% of a compound of Example 1 was prepared as follows:

| wt % | Compound | INCI name | Supplier |
|---|---|---|---|
| Part A | | | |
| 2.00 | PARSOL MCX | Octyl methoxycinnamate | 1 |
| 2.00 | Product of Example 1 | | |
| 3.00 | PARSOL 1789 | 4-tert. Butyl-4'-methoxy-dibenzoyl-methane | 1 |
| 12.00 | CETIOL LC | Coco-caprylate/caprate | 8 |
| 4.00 | DERMOL185 | Isostearyl neopentanoate | 9 |
| 0.25 | Diethylenegly-colmonostearate | PEG-2 -stearate | 4 |
| 1.00 | Cetylalcohol | Cetylalcohol | |
| 0.25 | MPOB/PPOB | Methyl-propylparabene | |
| 0.10 | EDTA BD | EDTA-sodium salt | 5 |
| 1.00 | AMPHISOL DEA | Diethanolamine cetylphosphate | 1 |
| Part B | | | |
| 20.00 | PERMULENE TR-1 (+%) | Acrylate C10—C30 Alkylacrylate | 7 |
| 48.60 | Deionized Water | Deionized Water | |
| 5.00 | Propyleneglycol | 1,2-Propanediol | |
| 0.80 | KOH (10%) | Potassium hydroxide | |

INCI: International Nomenclature Cosmetic Ingredients

Part A was heated in a reactor to 85° C. Part B was slowly added within 10 minutes, followed by addition of KOH, cooling and degassing of the emulsion.

Example 11

A broad spectrum sunscreen lotion containing 4% of a compound of Example 1 was prepared as follows:

| wt % | Compound | INCI name | Supplier |
|---|---|---|---|
| | | Part A | |
| 3.00 | PARSOL MCX | Octyl methoxycinnamate | 1 |
| 4.00 | Product of Example 1 | | |
| 3.00 | PARSOL 500 | 4-Methylbenzylidene camphor | 1 |
| 4.00 | PARSOL 1789 | 4-tert. Butyl-4'-methoxy-dibenzoyl-methane | 1 |
| 2.00 | Glyceryl monostearate | Glyceryl stearate | |
| 2.00 | Cetyl alcohol extra | Cetyl alcohol | |
| 2.00 | GANEX V-220 | PVP/Eicosene copolymer | 10 |
| 4.00 | CERAPHYL 375 | Isostearyl neopentanoate | 10 |
| 4.00 | CERAPHYL 847 | Octyldodecyl stearoyl stearate | 10 |
| 2.00 | AMPHISOL K | Potassium cetylphosphate | 1 |
| 0.10 | EDTA BD | Disodium EDTA | 5 |
| 0.60 | PHENONIP | Phenoxyethanol & Methyl-, Ethyl-, Propyl- & Butyl-paraben | 6 |
| | | Part B | |
| 11.15 | Deionized Water | Deionized Water | |
| 50.00 | CARBOPOL 934 1% solution | Carbomer | 7 |
| 5.00 | Propyleneglycol | 1,2- Propanediol | |
| 0.15 | NIPAGIN M | Methylparaben | 6 |
| 3.00 | KOH (10%) | Potassium hydroxide | |
| q.s. | Perfume oil | Fragrance | |

Part A was heated in a reactor to 85° C. Then homogeneous Part B was added followed by addition of preheated KOH (75° C.), cooling and degassing of the emulsion.

Example 12

A broad spectrum sunscreen cream containing 4% of the product described in Example 5 was prepared as set forth below. The cream has a low skin penetration quality:

| wt % | Compound | INCI name | Supplier |
|---|---|---|---|
| | | Part A | |
| 8.00 | PARSOL SLX | Dimethico-diethylbenzalmalonate | 1 |
| 4.00 | Product of Ex. 5 | | |
| 6.00 | T-COTE 031 | Titanium Dioxide & Dimethicone | 3 |
| 10.00 | ESTOL GTEH 3609 | Trioctanoin | 4 |
| 1.00 | Cetyl Alcohol | Cetyl Alcohol | |
| 4.00 | ESTOL GMM 3650 | Glyceryl Myristate | 4 |
| 0.05 | Butylated Hydroxytoluene BHT | | |
| 0.10 | EDTA BD | Disodium EDTA | 5 |
| 0.60 | PHENONIP | Phenoxyethanol & Methyl-, Ethyl- Propyl- & Butyl-paraben | 6 |
| 2.00 | AMPHISOL K | Potassium Cetyl Phosphate | 1 |
| | | Part B | |
| 50.75 | Deionized Water | Deionized Water | |
| 10.00 | CARBOPOL 980 1% solution | Carbomer 980 | 7 |

| wt % | Compound | INCI name | Supplier |
|---|---|---|---|
| 3.00 | Glycerin | Glycerin | |
| | | Part C | |
| 0.50 | KOH 10 % solution | Potassium Hydroxide | |
| q.s | Perfume Oil | Fragrance | 2 |

Part A was heated to 85° C. while stirring and then mixed for 30 seconds with a turbine at 8000 t/minutes. When homogeneous, Parts B and C were pre-heated to 75° C. and added to Part A. The mixture was cooled to 40° C. and Part D was added. The water loss was compensated and stirring was continued while cooling to ambient temperature. Then the mixture was mixed for 30 seconds with a turbine at 8000 t/minute.

Suppliers
1) F. HOFFMANN-LA ROCHE LTD, CH-4070 Basel/Switzerland
2) GIVAUDAN-ROURE SA, F-95101 Argenteuil-Paris/France
3) SUNSMART, Wainscott, N.Y. 11975/USA
4) UNICHEMA CHEMIE GmbH, D-4240 Emmerich/Germany
5) BASF AG, D-6700 Ludwigshafen/Germany
6) NIPA LABORATORIES LTD, Mid Glam. -CF38 2SN/England
7) B.F. GOODRICH COMPANY, Brecksville, Ohio 44141/USA
8) HENKEL K.G, Düsseldorf/Germany
9) BERNEL Chemical Co. INC. Englewood, N.J. USA
10) International Specialty Products ISP The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of formula I:

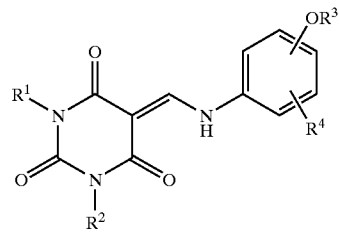

wherein
$R^1$ and $R^2$ are isopropyl;
$R^3$ is hydrogen, $C_1$–$C_{18}$ alkyl, $C_2$–$C_{18}$ alkyl in which at least one methylene group is replaced by oxygen, $C_1$–$C_{18}$ alkyl carbonyl, $C_3$–$C_{18}$ alkenyl, or $C_3$–$C_{18}$ alkynyl; and
$R^4$ is hydrogen, $C_1$–$C_8$ alkyl or a group $OR^3$.

2. A compound according to claim 1 wherein $R^4$ is hydrogen or hydroxy.

3. A compound according to claim 1 wherein $OR^3$ is in the para position and $R^3$ is 2-ethyl hexyl.

4. A compound according to claim 1 wherein the compound is selected from the group consisting of 5-{[4-(2-ethyl-hexyloxy)-phenylamine]-methylene}-1,3-diisopropylpyrimidine-2,4,6-trione, 5-{(4-propargyloxy-phenylamine)-methylene}-1,3-diisopropyl-pyrimidine-2,4,6-trione, 5-{(2,4-dihydroxy-phenylamine)-methylene}-1,3-diisopropyl-pyrimidine-2,4,6-trione, 5-{(4-capryloxy-phenylamine)-methylene}1,3-diisopropyl-pyrimidine-2,4,6-trione, 5-{[(2,4-Bis-capryloxyy)-phenylamine])methylene}-1,3-diisopropyl-pyrimidine-2,4,6-trione, and 5[(2-hydroxy-4-capryloxy)-phenylamine])-methylene}-1,3-diisopropyl-pyrimidine-2,4,6-trione.

5. A light screening composition comprising a compound according to claim 1.

6. A light screening composition according to claim 5 further comprising a screening agent selected from the group consisting of UV-A screening agents, UV-B screening agents, and mixtures thereof.

7. A light screening composition comprising a compound of formula I according to claim 1 in combination with a cosmetic base.

8. A method for protecting a surface of a substrate from ultraviolet light comprising applying to a surface of a substrate a UV-blocking amount of a light screening composition comprising a cosmetic base and a compound of formula I according to claim 1.

9. A compound of formula I according to claim 1 wherein $R^3$ is $C_1$–$C_8$ alkyl.

10. A compound of formula I:

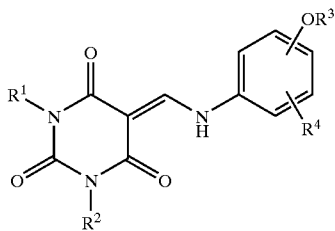

I wherein $R^1$ and $R^2$ are isopropyl;

$R^3$ is hydrogen, $C_1$–$C_{18}$ alkyl, $C_2$–$C_{18}$ alkyl in which at least one methylene group is replaced by oxygen, $C_1$–$C_{18}$ alkyl carbonyl, $C_3$–$C_{18}$ alkenyl, or $C_3$–$C_{18}$ alkynyl; and $R^4$ is $C_1$–$C_8$ alkyl or a group $OR^3$.

11. A compound according to claim 10 wherein $R_4$ is hydroxy.

12. A compound according to claim 10 wherein $OR^3$ is in the para position and $R_3$ is 2-ethyl hexyl.

13. A compound; according to claim 10 wherein the compound is selected from the group consisting of 5-{(2,4-dihydroxy-phenylamine)-methylene}-1,3-diisopropyl-pyrimidine-2,4,6-trione, 5-{[(2,4-Bis-capryloxy)-phenylamine])-methylene}-1,3-diisopropyl-pyrimidine-2,4,6-trione, and 5-{[(2-hydroxy-4-capryloxy)-phenylamine])-methylene}-1,3-diisopropyl-pyrimidine-2,4,6-trione.

14. A light screening composition comprising a compound according to claim 10.

15. A light screening composition according to claim 14 further comprising a screening agent selected from the group consisting of UV-A screening agents, UV-B screening agents, and mixtures thereof.

16. A light screening composition comprising a compound of formula I according to claim 10 in combination with a cosmetic base.

17. A method for protecting a surface of a substrate from ultraviolet light comprising applying to a surface of a substrate a UV-blocking amount of a light screening composition comprising a cosmetic base and a compound of formula I according to claim 10.

18. A compound of formula I according to claim 10 wherein $R^3$ is $C_1$–$C_8$ alkyl.

* * * * *